United States Patent [19]

Wong

[11] Patent Number: 4,687,442
[45] Date of Patent: Aug. 18, 1987

[54] SURGICAL ARTICULATOR APPARATUS AND METHOD

[76] Inventor: Brian W. Wong, 1672 Toyon Ct., San Mateo, Calif. 94403

[21] Appl. No.: 729,303

[22] Filed: May 1, 1985

[51] Int. Cl.$^4$ .............................................. A61C 11/00
[52] U.S. Cl. ........................................ 433/63; 433/60; 433/64; 433/65
[58] Field of Search ............... 433/63, 64, 60, 65, 433/54, 55, 56, 57, 58, 59, 61, 62, 66, 67

[56] References Cited

U.S. PATENT DOCUMENTS

| 2,550,043 | 4/1951 | Lautour | 433/63 |
| 2,608,762 | 9/1952 | Fox | 433/63 |
| 2,644,233 | 7/1953 | Shmukler et al. | 433/63 |
| 2,754,588 | 7/1956 | Cordell | 433/63 |
| 2,959,857 | 11/1960 | Stoll | 433/61 |
| 3,067,515 | 12/1962 | Wilkinson | 433/60 |
| 3,885,311 | 5/1975 | Lawler et al. | 433/65 |
| 4,315,740 | 2/1982 | Mercer et al. | 433/63 |
| 4,358,269 | 11/1982 | Hay et al. | 433/60 |
| 4,391,589 | 7/1983 | Monfredo et al. | 433/63 |
| 4,468,198 | 8/1984 | Kataoka et al. | 433/63 |
| 4,504,226 | 3/1985 | Gordon | 433/63 |

Primary Examiner—John J. Wilson
Attorney, Agent, or Firm—Fitch, Even, Tabin & Flannery

[57] ABSTRACT

An apparatus for holding and manipulating a dental cast in a dental articulator and a method for using this apparatus in combination with an occlusal plane table to adjust and record the positions of the teeth before and after repositioning of the dental cast is disclosed. The apparatus enables the dental cast to be translated in a plane and to be rotated about one or more of a plurality of axes which are chosen to correspond to the axes about which adjustments are made during dental surgery. The occlusal plane table includes a removable grid which provides a reference system with which to measure the adjustments to the position of the dental cast without the need to calibrate the various translational and rotational controls for each dental cast.

20 Claims, 15 Drawing Figures

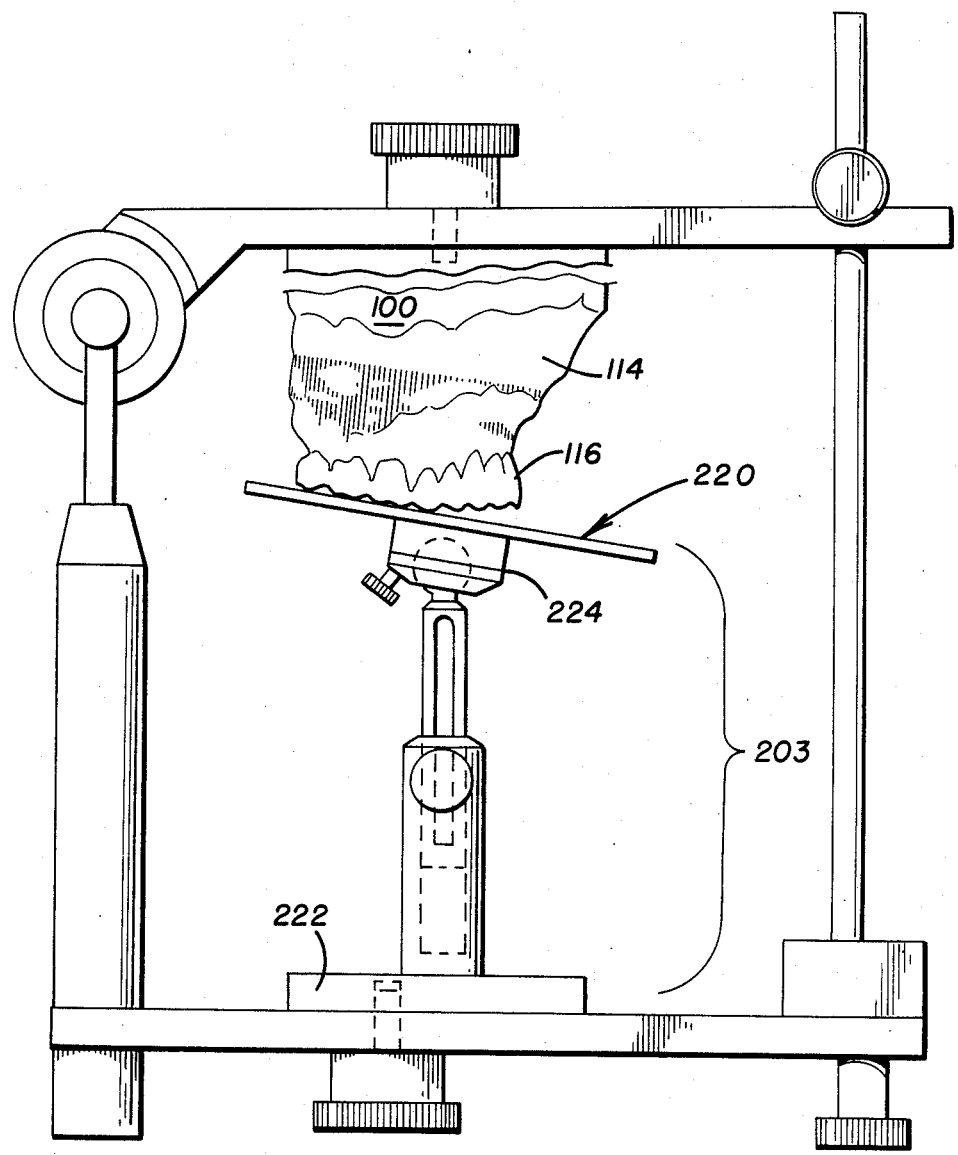
FIGURE II

SURGICAL ARTICULATOR APPARATUS AND METHOD

BACKGROUND OF THE INVENTION

This is a co-pending patent application to contemporaneously filed patent application Ser. No. 729,276, now U.S. Pat. No. 4,624,639 issued 11/25/76, for an Adjustable Occlusal Plane Table which is incorporated herein by reference. The present invention relates to orthognathic setups and more particularly to an apparatus and method for use with a dental articulator to adjust dental arch models mounted in the articulator.

Dental surgery has achieved remarkable success with many patients. Although sometimes quite complicated and painful, the results achieved have enormous beneficial functional and aesthetic effects. Patients who formerly had gross malocclusions which distorted their appearance and made even the simple act of chewing food a chore have achieved a normal appearance and normal chewing process through dental surgery.

A common surgical procedure for correcting malocclusions involves repositioning the maxillary (upper jaw) and mandible (lower jaw) with respect to the patient's skull. This is accomplished with the aid of two splints. The first splint is used to set the correct position of the maxillary by reference to the uncorrected position of the mandible. The second splint is used to set the position of the mandible by reference to the corrected maxillary position. The surgical procedure is carried out as follows. First, the maxillary is cut from the supporting bone so that it may be repositioned. The first splint is inserted between the patients teeth and the maxillary is then wired to the bone in its new position while its position is fixed by the splint. The first splint is then removed and the mandible is cut from its supporting bone so that it may be repositioned. The second splint is then inserted between the teeth and the mandible is wired to the bone in its new position.

The two surgical splints are made with the aid of a dental articulator from casts (arch models) made of the patient's teeth. The dental casts for the maxillary and mandible are first mounted relative to one another in a conventional manner in the articulator with respect to the hinge axis of the articulator. That is, the arch models are mounted so as to approximate as closely as possible, the position of the patient's teeth with respect to the hinge axis of the patient. The first splint is made after the maxillary dental cast is repositioned to its desired new position. This new position is chosen after studying X-rays of the patient's skull, in addition to a visual examination of the patient's anatomical characteristics. The first splint is then made by placing a moldable material between the repositioned maxillary dental cast and the mandible dental cast and then allowing it to harden. The first splint is then removed. The mandible dental cast is then repositioned to its desired position and the second splint constructed in an analogous manner.

The prior art apparatus and methods for repositioning each of the dental casts from the their current positions to their desired positions are both time consuming and inaccurate. In one prior art method, a series of grid lines are drawn on one of the dental casts, usually the maxillary. An estimate of the positional changes is then made and a wedge portion of the support of the dental cast cut out to create this positional change. The cast is then glued back together. A quantitative measurement of the extent of position adjustment of the maxillary arch model is obtained by measuring the remaining grid lines on the dental cast. Since the grid lines used to make these cuts are drawn by hand, inaccuracies result. Greater inaccuracies result from the fact that the wedge being cut out is substantially above the plane of occlusion of the arch model. Thus, a position change made to the teeth in this manner usually will also create unintended and undesirable other position changes. Furthermore, fine adjustments in the positioning are difficult to make. In addition, multiple casts are needed when this method is used, so that one set of dental casts can be left unaltered to preserve a record of the original position of the patients teeth.

One attempt to improve on the above prior art method is disclosed in U.S. Pat. No. 4,391,589 to Monfredo, et al. This apparatus eliminated the need to cut and glue the support members, by providing a support system for the dental casts which included translational and rotational means for repositioning the dental casts. This apparatus has three problems. First, an operator cannot conveniently use the apparatus to precisely move one of the dental arches to a predetermined position relative to the other dental arch using the dial settings provided. Although the apparatus has dials which indicate the angle through which the dental cast is rotated, these dials are of little use in making a precise change in the position of the dental arch which is located at the end of the dental cast. When the dental cast is rotated about one of the two rotational axes in the Monfredo, et al. apparatus, the dental arch is translated in at least two directions by an amount which depends both on the angle of rotation indicated by the dial on the apparatus and on the distance from the axis of rotation to the dental arch. This distance varies with different dental set-ups. Consequently, one would have to calibrate each dental set-up to take into account this distance and perform a displacement calculation for each rotational movement. This is not practical. As a result, in practice, the movements must be made visually which introduces inaccuracies.

Second, the axes chosen for rotation in the Monfredo, et al. apparatus make it difficult and time consuming to move the teeth to a predetermined location. Even if the setup is calibrated to the particular dental casts, a rotation about one of the axes provided in this prior art apparatus results in unintended and undesirable translational movements of the teeth in addition to the desired rotational movement. To compensate for these additional movements, additional displacement adjustments must be made. The changes in these multiaxis dial settings to accomplish these adjustments depend on the magnitude of the rotation made as well as the distance from the teeth to the axis of rotation. Hence, these adjustments must either be made by using a calibration procedure requiring calculations to be made for each movement or by making visual adjustments which are inaccurate. In either case, the difficulty and time required to reposition the dental cast is significant.

Third, a record of the final position of the teeth is difficult to construct using the Monfredo, et al. apparatus, since the relationship between the actual movement of the teeth and the dial settings depends upon the dimensions of the dental cast and its position on the support. To construct such a record requires a lengthy calibration procedure for each setup.

SUMMARY OF THE INVENTION

The present invention consists of an apparatus for holding and manipulating the position of a dental cast in a dental articulator and a method for using this apparatus in combination with an occlusal table to adjust and record the positions of the teeth before and after repositioning of the dental casts. The apparatus includes means for translating the dental cast in a substantially horizontal plane and for causing it to rotate about one or more of a plurality of axes. The dental cast is supported on a planar adjustment means which provides the means for translating the dental cast and for rotating the dental cast about one of a plurality of axes which are perpendicular to the plane of adjustment and which substantially pass through predetermined points on the dental arch about which adjustments are often made during surgery. The anterior portion of the planar adjustment means may be adjusted so as to cause the dental cast to rotate vertically about an axis passing through the center of the hinge axis of the articulator for making vertical adjustments in the position of the anterior portion of said dental arch. The posterior portion of the planar adjustment means may be adjusted so as to cause the dental cast to rotate about an axis which is substantially parallel to an axis either defined by the left row of teeth on said dental arch or an axis defined by the right row of teeth on said dental arch.

The method for recording the repositioning of the dental cast employs an occlusal plane table having a removable grid. The occlusal plane table replaces one of the dental casts during the repositioning procedure and is designed to maintain the original plane of occlusion as a reference plane for enabling later position adjustments of the remaining dental cast to be measured, thereby eliminating the need to calibrate the various translational and rotational controls for each dental cast.

Consequently, it is an object of the present invention to provide an improved dental cast positioning apparatus and method for use with a dental articulator which enables translational and rotational adjustment of the position of a dental cast in an articulator while minimizing the need for compensating adjustments to the position of the dental cast in axes that are not being adjusted.

It is a further object of the present invention to provide means for making precise predetermined movements of a selected dental arch with respect to a patient's plane of occlusion.

It is a still further object of the present invention to enable an accurate record of the old and new positions of the teeth.

These and other objects of the present invention will be apparent from the following detailed description of the present invention and the accompanying drawings.

DETAILED DESCRIPTION OF THE DRAWINGS

FIG. 11 shows the placement of the occlusal table during an alignment procedure involving the maxillary dental cast.

DETAILED DESCRIPTION OF THE INVENTION

The present invention overcomes the problems of the prior art by providing a dental arch support in an articulator in which position readjustments resulting from rotating the dental cast with respect to the patient's original plane of occlusion are minimized and by providing an alignment method in which the position of the dental cast relative to a fixed set of coordinates is used instead of measuring the displacements by dial settings on the articulator which are difficult to calibrate in terms of actual dental cast movement. The closest prior art provided only two axes about which rotations can be made. The preferred embodiment of the present invention provides 7 axes. Also unlike the prior art, these axes are carefully chosen to correspond to the type of motions actually used in realigning the patients teeth.

Figure 1A:
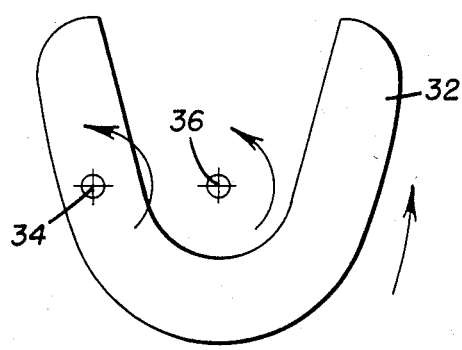
FIG. 1a and 1b illustrates rotational movements used in repositioning the dental arches.

Referring to FIG. 1(a), a common realignment requires that the teeth be rotated on a horizontal plane about a point 34 in the dental arch shown at 32. To accomplish this realignment using the prior art methods and apparatus, a rotation was made about an axis passing through the point shown at 36. Not only did this result in the dental arch being rotated as desired, but also it resulted in the point 34 on the dental arch 32 being translated down and to the right in the FIGURE. This undesired translation had to be removed by readjusting the dental cast to a new position in which point 34 was returned as close as possible to its starting position. Additional trial and error translational adjustments were required to accomplish this result. The apparatus of the present invention overcomes this problem by placing one of the axes about which rotations can be made at point 34. Hence the dental arch may be rotated about 34 without introducing undesired additional movements.

Figure 1B:
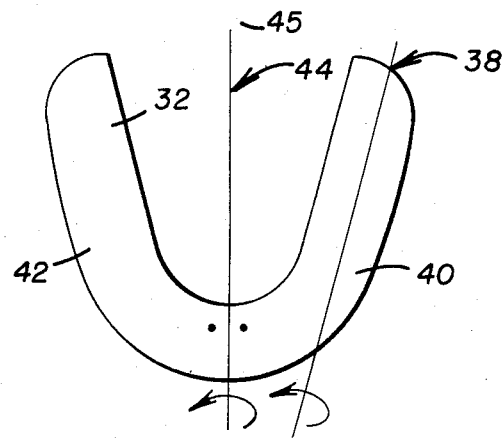

Similarly, a rotation to realign the patients teeth in a vertical plane about an axis passing through the line of teeth (axis 38 shown in FIG. 1(b)) is commonly used in dental surgery. The prior art apparatus only provided an axis 44, which passed through a plate in the articulator that the upper portion of the dental cast was attached to, and an axis 45 at right angles to this axis to accomplish this rotation. To accomplish this rotation, rotations were made about each of these axes and then the dental cast was translated to correct for the undesired changes in position introduced by these rotations. The apparatus of the present invention provides axes which run substantially through the rows of teeth in question, and hence this type of rotation may be accomplished with a single adjustment.

Figure 2:
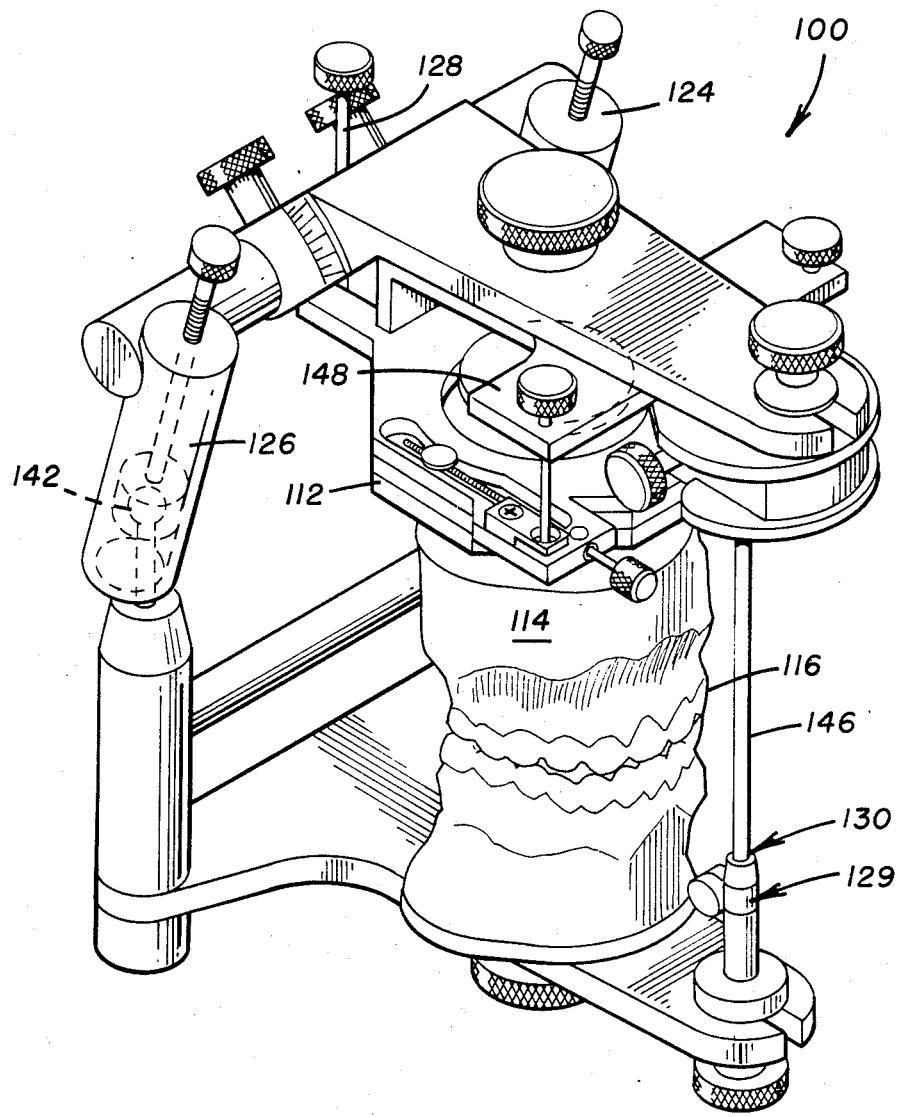
FIG. 2 is a perspective view of an apparatus according to the present invention.
Figure 3:
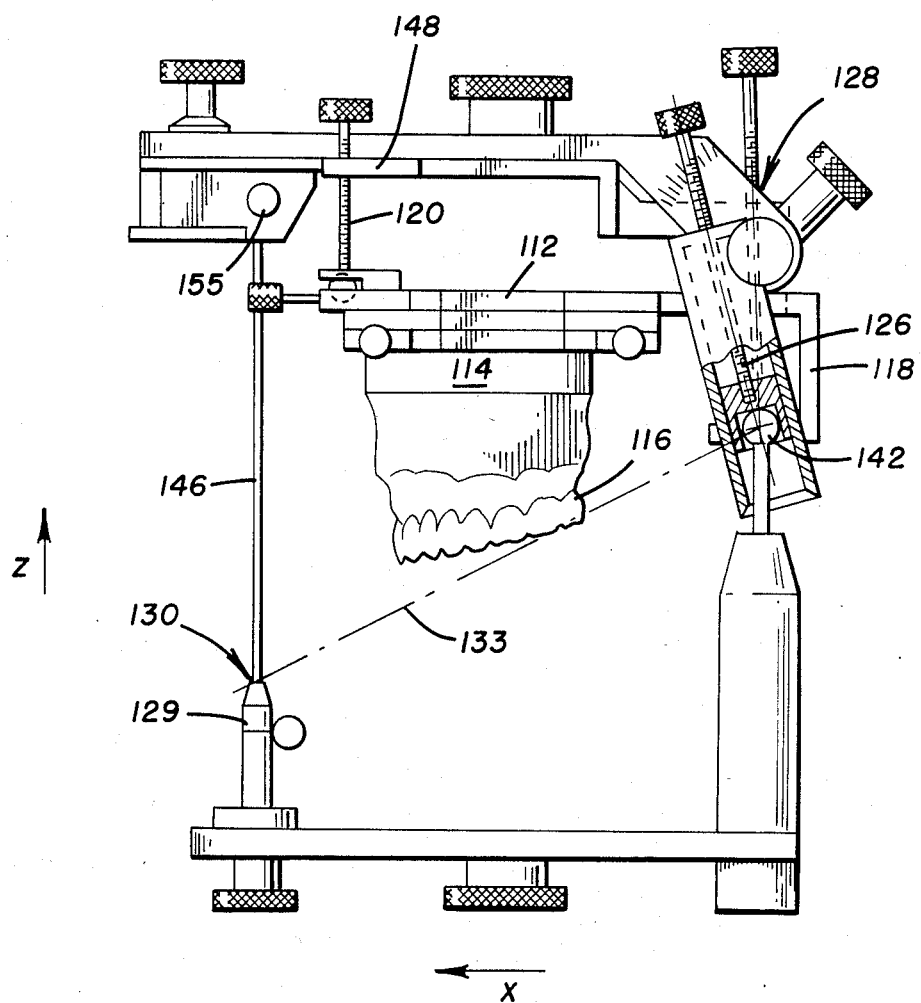
FIG. 3 is a side view of the apparatus shown in FIG. 2.
Figure 4:
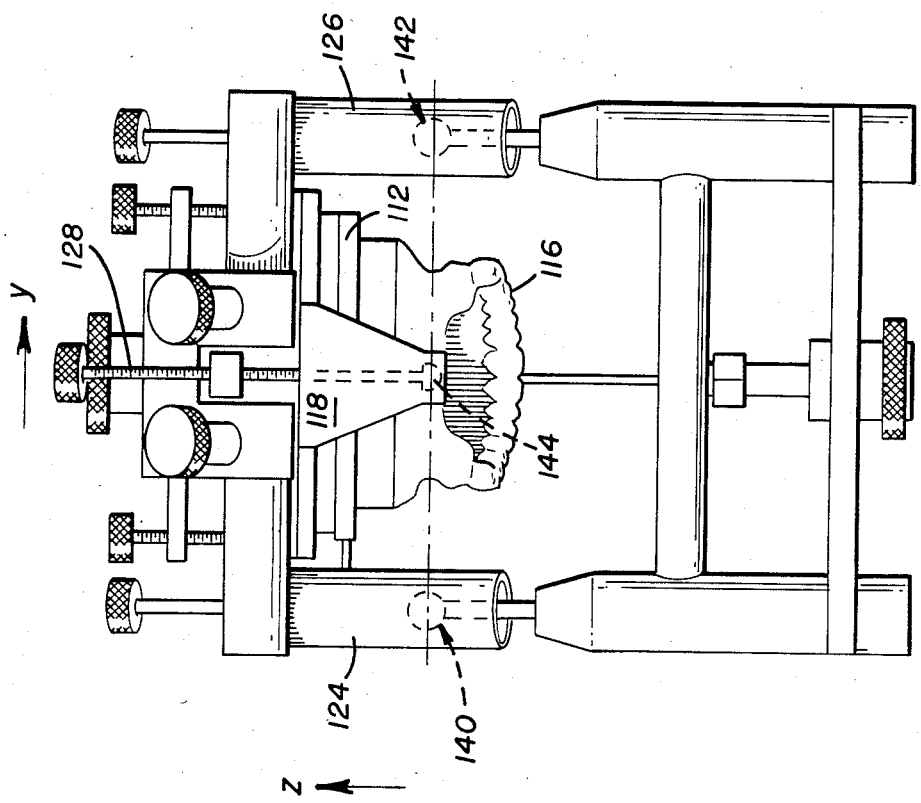
FIG. 4 is a rear view of the apparatus shown in FIG. 2.

An apparatus according to the present invention is shown in perspective view at 100 in FIG. 2 and in side and rear views in FIGS. 3 and 4. The mandibular dental cast has been removed from the apparatus in FIGS. 3 and 4 for clarity. A dental cast 114 including a dental arch model 116 representing the teeth of the patient is attached to a planar adjustment means 112. Planar adjustment means 112 is in turn attached to a plate 148. Plate 148 also is used to attach the apparatus to the top plate of the articulator. The anterior portion of planar support means 112 is supported by two linear support members 120 and 122 whose length may be varied. The posterior end of the planar adjustment means is supported by pivotal adjustment support 128 which causes the posterior portion of the planar adjustment means 118 to lie substantially on the center point 144 of the hinge axis which passes through points 140 and 142. The plate 148 is supported by two linear members 124 and 126 whose length can be varied and by an incisal pin 146 which is connected to the anterior end of said plate 148 at 155 and which rests freely on the articulator base at 130.

The planar adjustment means 112 allows the operator to adjust the position of the dental cast in a plane parallel to the planar adjustment means and to cause the dental cast to rotate about a number of axes which are perpendicular to the plane of the planar adjustment means. These axes substantially pass through the points on the dental arch at which rotational adjustments are often made during surgery.

Figure 5:
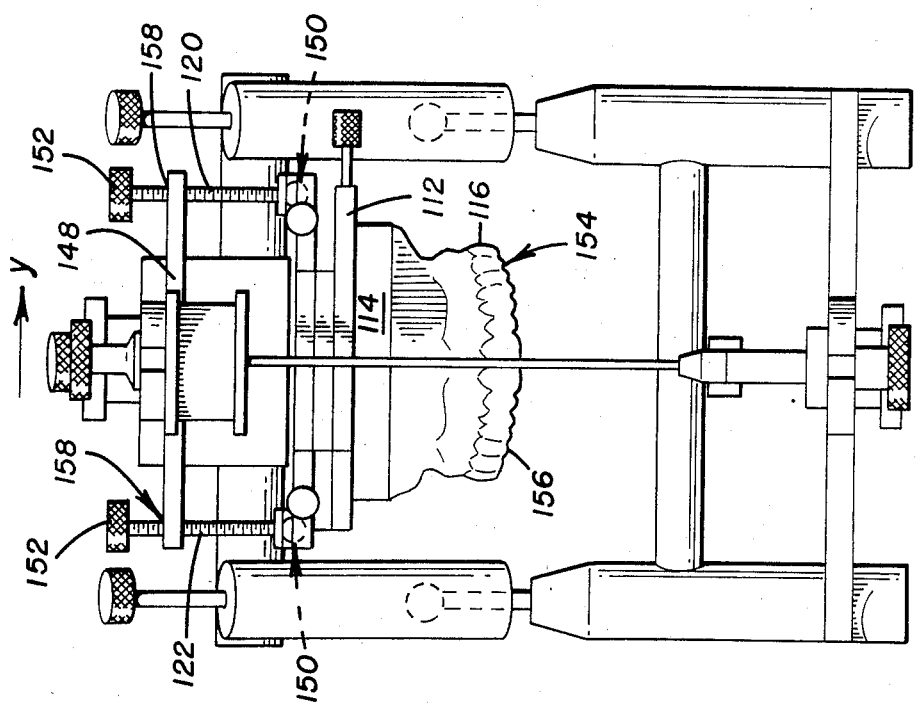
FIG. 5 is a front view of means for adjusting the anterior portion of a dental cast according to the present invention.

Referring to FIG. 5, for vertical adjustment of the position of arch model 116 the anterior portion of the arch model 116 may be adjusted by changing the lengths of the support members 120 and 122. To raise or lower the anterior portion of the arch model, the support members 120 and 122 are lengthened or shortened by an equal amount. One side of the arch model may also be raised or lowered relative to the other side by shortening or lengthening the appropriate support. For example, the right side 154 may be raised without changing the height of the left side 156 by shortening the support member 120. In the preferred embodiment, the support members 120, 122 are worms which are rotatably mounted to the planar adjustment means 112 by ball joints 150 and threadably engage the plate 148 at corresponding opposite points 158. The engagement of one of the worms with the plate 148 includes a threaded adapter mounted in a slot to enable a limited amount of motion parallel to plate 148 to accommodate the change in angle which results when the two supports 120, 122 are adjusted to have unequal lengths. The length of a support 120, 122 is changed by rotating an adjustment knob 152 mounted at the top of each worm support 120, 122. The ball joints 150 provide means for accommodating the change in angle between the support and the planar adjustment means which results when the length of one of the supports is changed without a change in the other support.

The beneficial aspect of this structure is that each of the supports 120 and 122 affect only the height of one side of the arch model 116, the side which is closest to support in question. No compensating adjustment in the position of the other side of arch model 116 is necessary. This is because when one of the supports is adjusted, the planar adjustment means 112 pivots about point 144.

Figure 6A:
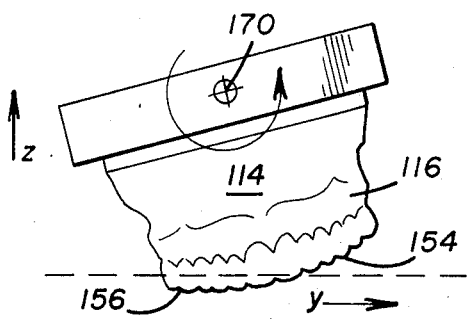
FIG. 6a and 6b illustrates resultant rotational movement of a dental cast using the prior art apparatus and using the apparatus of the present invention.

This is a significant improvement over the prior art, wherein changes in the position of one side of the anterior portion of the arch model relative to the other side were accomplished by rotating the dental cast about an axis 170 in the middle of the dental cast, as illustrated in FIG. 6(a). In addition to raising the right side when the dental cast is rotated in a counterclockwise manner, this results in the left side 156 being lowered, and the arch model being shifted a significant amount in the y-direction as indicated by the arrow in the FIG. 6(a). To compensate for these undesired shifts, additional adjustments must be made in the y position and the height of the dental cast (i.e. the z direction). This was a time consuming and imprecise step in the prior art.

Figure 6B:
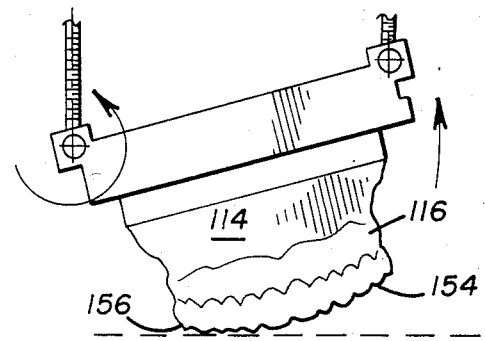

The present invention minimizes this time consuming readjustment. When only one support is shortened, as shown in FIG. 6(b), at most a small displacement results in the y-direction. There is no additional displacement in the z-direction. The magnitude of this displacement is also significantly less than the corresponding displacement using the prior art apparatus.

Referring again to FIG. 5, if both the supports 120 and 122 are shortened or lengthened by the same amount, the planar adjustment means will rotate about the hinge axis, since the posterior portion of the planar adjustment means is connected to a pivot point 144 positioned on the hinge axis. This raises the anterior portion of dental arch relative to the posterior portion by causing the dental arch to rotate about the hinge axis. This closely models the types of position adjustments performed during surgery. In the closest prior art, this change in the anterior-posterior positioning is accomplished by rotation about an arbitrary axis which is not coincident with the hinge axis. As a result, the dental cast must be repositioned with respect to the hinge axis after the anterior-posterior adjustment.

Figure 7:
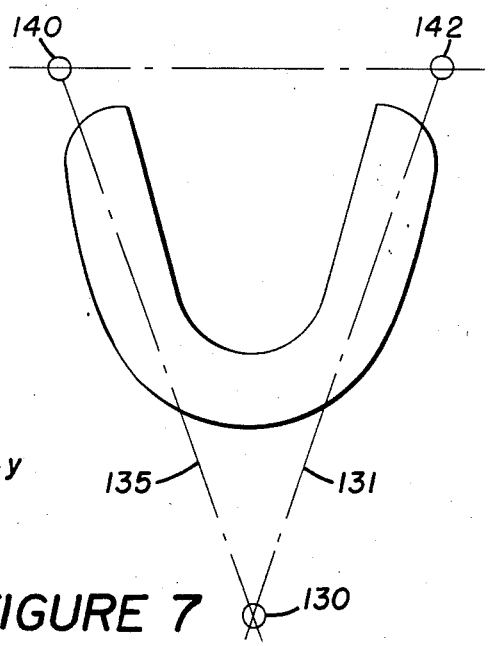
FIG. 7 illustrates two axes of rotation passing through the line of the teeth in the dental arch which are created by the apparatus shown in FIG. 2.

As illustrated in FIGS. 3 and 7, the dental arch may also be rotated about an axis running through the row of teeth on either side of the dental arch by changing the length of one of the posterior support members 124 or 126. A change in one of these supports results in the plate 148, and hence the arch model 116, rotating about an axis lying in the plane 133 defined by the hinge axis and the point where incisal pin 130 contacts the incisal table 129. These axes are shown at 131 and 135 in FIG. 7. In the prior art, such a rotation could only be carried out by making a time-consuming series of adjustments involving rotating the dental cast about two axes and then repositioning it by displacements in the x, y, and z directions.

If the posterior adjustment supports 124, 126 are both lengthened, the dental cast will rotate about the point at which the incisal pin meets the incisal table shown at 130. This causes the dental arch to move toward the rear of the apparatus in addition to rotating about this axis. This movement may be substantially reduced by inclining the posterior support members 124, 126 a specific angular amount toward the front of the apparatus such that said supports are tangent to an arc centered at point 130.

Figure 8:
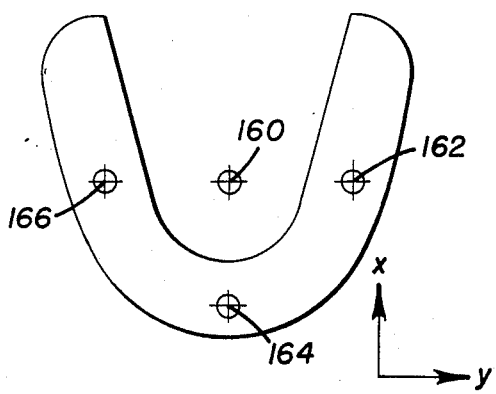
FIG. 8 illustrates the four axes of rotation passing through preselected points on the dental arch.

Translations in the x and y directions and rotations about axes perpendicular to the x-y plane are carried out by means of planar adjustment means 112. The closest prior art provides only one axis perpendicular to the x-y plane about which rotations could be made, and this axis was not placed over any of the teeth about which rotations are normally made during the adjustment procedure. As a result, to rotate the dental cast about an axis passing through the teeth shown at 162, 164, and 166 in FIG. 8, a rotation was first made about the axis shown at 160, and then compensating translating movements were made in the x and y directions. The present invention eliminates these time consuming compensating motions by placing axes about which rotations can be made at several points which lie substantially on the dental arch. In the preferred embodiment, axes passing through the three points shown at 162, 164, and 166 in FIG. 8 are provided.

Figures 9A, 9B:
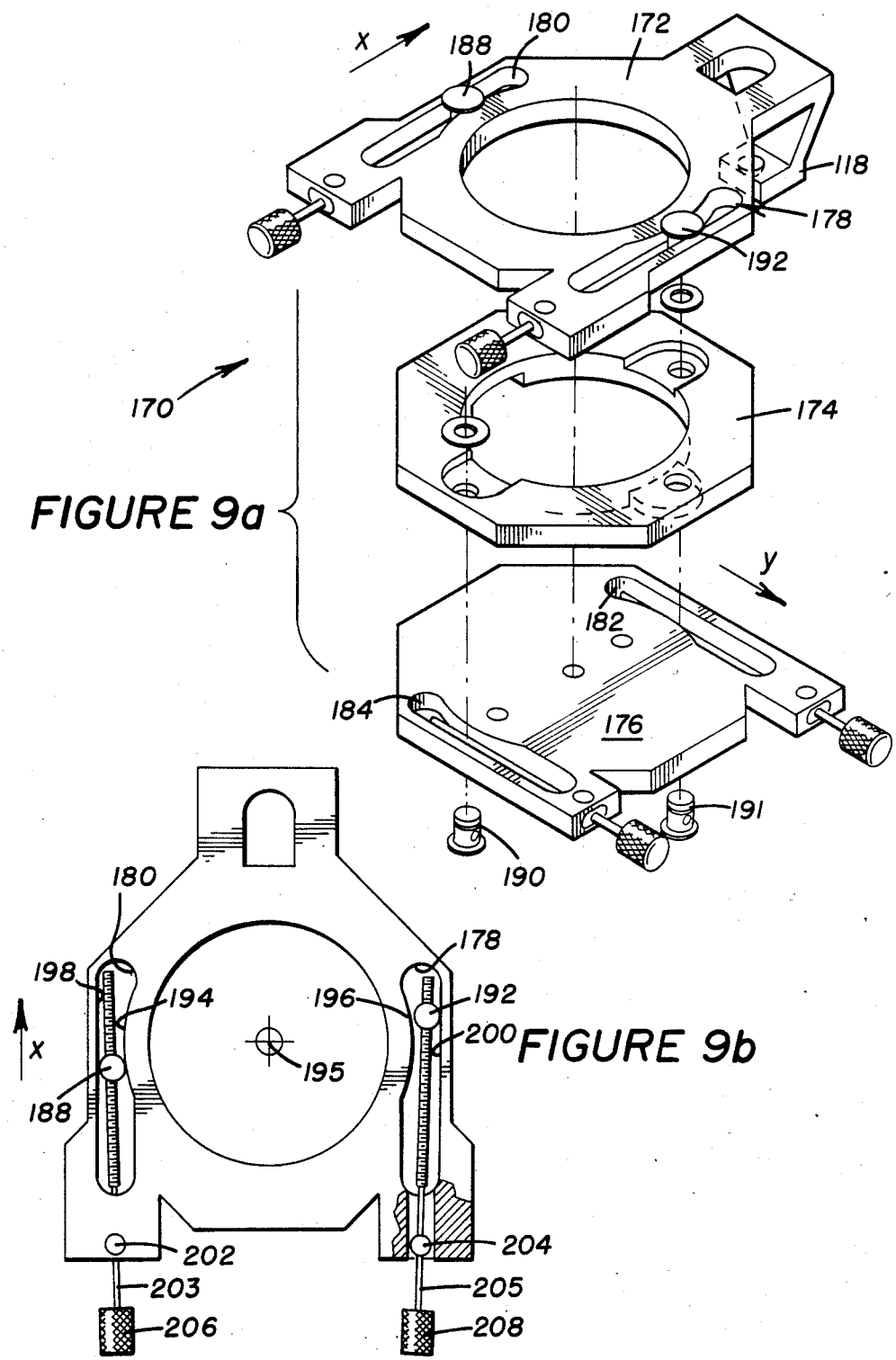
FIG. 9a and 9b is a drawing of the planar adjustment means used in an apparatus according to the present invention.

The preferred planar adjustment means 112 is shown at 170 in FIG. 9(a). It consists of three plates 172, 174, and 176 which are mounted parallel to one another. The outside plates 172 and 176 each contain two sets of cam surfaces shown at 178 and 180 on plate 172 and at 182 and 184 on plate 176. Each set of cam surfaces engages a cam follower which is mounted on the center plate 174 with its axis perpendicular to said center plate. The cam follower which engages the cam surfaces 180 is shown at 188. The cam follower 190 that engages cam surfaces 182 protrudes from the other side of the center plate 174. By adjusting the position of the top plate as described below, the dental cast may be translated in the x direction or rotated about an axis passing through either cam follower 188 or 192. Similarly, by adjusting the position of the bottom plate relative to the center plate, translations in the y direction or rotations about the axes passing through cam followers 190 and 191 may be made.

FIG. 9(b) shows a top view of plate 172. Each set of cam surfaces consists of a linear surface and an arcuate surface. The linear surfaces 198 and 200 are parallel to each other. The arcuate surfaces 194 and 196 have a common center shown at 195. The parallel surfaces are separated by a distance equal to the diameter of the circle containing the arcuate surfaces plus the diameter of the cam follower. When a cam follower is positioned at the closest point between the linear and arcuate surfaces it engages, it is in contact with both said surfaces. Cam follower 188 is so positioned in FIG. 10(b).

The position of the plate 172 relative to the center plate 174 is adjusted by setting the distance between each of the cam followers engaging the plate and a point on the plate associated with that cam follower. In the preferred embodiment, the position of cam follower 188 relative to a point 202 on plate 172 is set by a worm 203 which is rotatably mounted to said plate at 202 and which threadably engages cam follower 188. The distance between cam follower 188 and point 202 is set by turning a knob 206 attached to said worm. Similarly, the distance between cam follower 192 and point 204 on plate 172 is set by adjusting a worm 205 using knob 208.

Figure 10A:
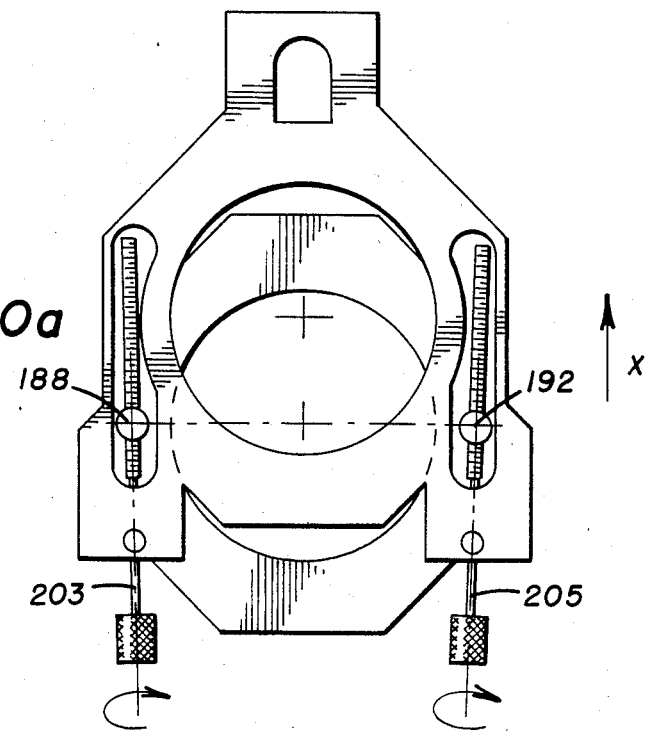
FIG. 10a and 10b illustrates the use of the planar adjustment means shown in FIG. 9 to perform translational and rotational movements of a dental cast.
Figure 10B:
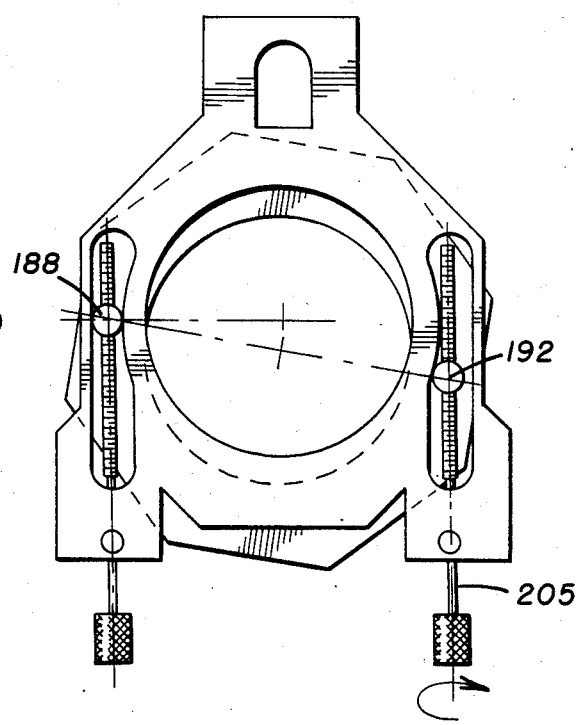

FIG. 10 illustrates various movements using plate 172. To translate the plate in the x direction, the worms 203 and 205 are both adjusted by the same amount. Each cam follower is in contact with its associated linear surface as shown in FIG. 10(a). To rotate about cam follower 188, worm 205 is adjusted which causes the plate to rotate about cam follower 188. The maximum rotational adjustment is obtained when a cam follower is located at the point of closest approach between the linear and arcuate surfaces it engages as shown in FIG. 10(b). Rotations about the second cam follower 192 can be made in an analogous manner.

The apparatus of the present invention is preferably used in conjunction with an occlusal plane table which facilitates the measuring and recording of the displacements and rotations needed to reposition the patients teeth to eliminate the current malocclusion. The occlusal plane table is the subject of a separate co-pending patent application, Ser. No. 729,276, which is now U.S. Pat. No. 4,624,659 which was incorporated by reference above.

The arch model repositioning method according to the present invention, in conjunction with said occlusal plane table, is carried out as follows. First, the dental casts are aligned in the articulator in the their current positions of malocclusion using conventional setup procedures such that the hinge axis of the articulator corresponds to the true axis of the patient. One of the casts is then removed and the occlusal plane table 203 put in its place, as shown in FIG. 11. The occlusal plane table consists of a table surface 220 having a removeable grid pattern defined thereon, which in the preferred embodiment is graph paper having 1 mm spacing, a stand 222 and a means 224 for three dimensionally adjusting the position and angle of tilt of said table surface. The base of the stand 222 is located at the position of the dental cast which has been removed. As shown in FIG. 11, this is preferably the mandibular dental cast. The table surface 220 is adjusted to coincide with the plane of occlusion defined by arch model 116.

The position of the maxillary arch model 116 is then recorded with reference to the occlusal table grid by marking the locations of several of the teeth on said arch model on the grid and by recording the distance from the occlusal table to one or more of said teeth on said grid. The maxillary arch model is then repositioned to its new position using the various adjustments provided by the apparatus of the present invention. The repositioning is done by reference to X-rays of the patient's skull and after visual examination of the patient's anatomical features by the orthodontist when the impressions for the dental casts were made.

Since the grid located on surface 220 provides a reference with respect to the arch model 116, precise movements of the arch model can be made without reference to the actual calibration markings of the various worms used by the apparatus of the present invention to make the various rotations and translations. For example, if one side of the arch model is to be raised relative to the other side as illustrated in FIG. 6(b), the worm 120 shown in FIG. 5 would be turned so as to raise the dental arch at point 154. If this movement results in a translation of the dental arch, the translation is visually much more easily perceived and can be corrected by moving the dental cast using the planar adjustment means while observing the position of said arch model with respect to the occlusal plane table grid.

When the maxillary arch model has been repositioned as desired, its new position is recorded with respect to the grid in the same manner as its original position was recorded. These grid measurements are then archived, preferably by removing the grid, including the measurement markings, from surface 220, to provide a permanent record of the adjustments needed to realign the maxillary. Such a record was difficult to produce, even with the closest prior art devices, since the calibration markings of the various dials which controlled the movements of the arch models were not easily converted to the movements of the arch model needed to produce correct repositioning.

Once the maxillary arch model is correctly aligned, the occlusal plane table is removed and the mandibular arch model put in its place. The first surgical splint may then be made by placing an appropriate material between the two dental arch models and allowing it to harden.

The mandibular arch model is then repositioned with respect to the new position of the maxillary arch model to create proper occlusion between the maxillary and mandibular arch models, and a second or final surgical splint is then made.

Various modifications to the above described apparatus will be apparent to those skilled in the art without departing from the present invention as claimed. Accordingly, the scope of the present invention is defined by the following appended claims.

What is claimed is:

1. An apparatus for mainpulating a dental cast, including a dental articular having a horizontal hinge axis comprising:

planar adjustment means mounted on said articulator for supporting said dental cast and for enabling said dental cast to be translated in two substantially orthogonal directions parallel to a substantially horizontal plane of motion and for enabling said dental cast to be rotated about a selected one of a plurality of axes, each axis being perpendicular to said plane of motion and passing substantially through said dental arch at a predetermined point, said planar adjustment means including means for selecting and providing a fixed pivot point about each of said selected axes passing substantially through said dental arch.

2. An apparatus for manipulating a dental cast, including a dental arch representing the teeth, for use in a dental articulator having a horizontal hinge axis comprising:

planar adjustment means mounted on said articulator for supporting said dental cast and for enabling said dental cast to be translated in two substantially orthogonal directions parallel to a substantially horizontal plane of motion and for enabling said dental cast to be rotated about one of a plurality of axes, each axis being perpendicular to said plane of motion and passing substantially through said dental arch at a predetermined point, said planar adjustment means comprising:

a first plate including first, second, third, and fourth cam following means, said first and second cam following means having axes perpendicular to said first plate and protruding from the same side of said first plate, said axes substantially passing through said dental arch at first and second preselected points on said dental arch, third and fourth cam following means having axes perpendicular to said first plate and protruding from the opposite side of said first plate from said first and second cam following means and lying on a line which is perpendicular to the line joining said first and second cam following means, said third cam following means axis passing substantially through the center of the teeth of said dental arch, each of said cam following means having the same diameter;

a second plate mounted parallel to said first plate having a first linear cam surface and a first arcuate cam surface for engaging said first cam following means, a second linear cam surface and second arcuate cam surface for engaging said second cam following means; means for setting the distance between said first cam following means and a first predetermined point on said second plate, and for setting the distance between said second cam following means and a second predetermined point on said second plate, wherein said first and second linear cam surfaces are parallel to one another, said first and second arcuate surfaces have a common center lying equidistant from said first and second linear cam surfaces, the distance between said first and second linear cam surfaces being equal to the diameter of the circle containing said first and second arcuate surfaces plus the diameter of said cam following means;

a third plate mounted parallel to said first plate on the opposite side of said first plate from said second plate, having a third linear cam surface and a third arcuate cam surface for engaging said third cam following means; a fourth linear cam surface and fourth arcuate cam surface for engaging said fourth cam following means; means for setting the distance between said third cam following means and a third predetermined point on said third plate, and for setting the distance between said fourth cam following means and a fourth predetermined point on said third plate, wherein said third and fourth linear cam surfaces are parallel to one another, said third and fourth arcuate surfaces have a common center lying equidistant from said third and fourth linear cam surfaces, the distance between said third and fourth linear cam surfaces being equal to the diameter of the circle containing said third and fourth arcuate surfaces plus the diameter of said cam following means; and means for connecting said dental cast to said third plate.

3. The apparatus of claim 2 wherein each of said means for setting the distance between a cam following means and a predetermined point on the plate containing the cam surfaces engaged by said cam following means comprises a worm rotatably mounted on said plate and threadable engaged with said cam following means for displacing said plate relative to said cam following means upon rotation of said worm.

4. The apparatus of claim 2 wherein each said cam following means comprises a roller.

5. An apparatus for manipulating a dental cast including a dental arch representing the teeth for use in a dental articulator having a horizontal hinge axis and a base including an incisal table comprising:

planar adjustment means for supporting said dental cast and for enabling said dental cast to be translated in two substantially orthogonal directions parallel to a substantially horizontal plane of motion and for enabling said dental cast to be rotated about one of a plurality of axes, each axis being perpendicular to said plane of motion and passing substantially through said dental arch at a predetermined point;

posterior adjustment means mounted on said articulator and connected to said planar adjustment means for enabling said dental arch to be moved in a vertical direction and for enabling said dental cast to rotate about a right occlusion axis lying substantially along the right row of teeth of said dental arch and a left occlusion axis lying substantially along the left row of teeth of said dental arch; and anterior adjustment means connected to said planar adjustment means and to said posterior adjustment means for enabling said plane of motion of said planar adjustment means to be rotated about said hinge axis, for causing said said plane of motion to rotate about a first anterior axis substantially passing through the center of said hinge axis, and for enabling said plane of motion to be rotated about a second anterior axis passing substantially through the center of said hinge axis.

6. The apparatus of claim 5 wherein said planar adjustment means further comprises:

a first plate including first, second, third, and fourth cam following means, said first and second cam following means having axes perpendicular to said first plate and protruding from the same side of said first plate, said axes substantially passing through said dental arch at first and second preselected points on said dental arch, third and fourth cam following means having axes perpendicular to said first plate and protruding from the opposite side of said first plate from said first and second cam following means and lying on a line which is perpendicular to the line joining said first and second cam following means, said third cam following means axis passing substantially through the center of the teeth of said dental arch, each of said cam following means having the same diameter;

a second plate mounted parallel to said first plate having a first linear cam surface and a first arcuate cam surface for engaging said first cam following means, a second linear cam surface and second arcuate cam surface for engaging said second cam following means; means for setting the distance between said first cam following means and a first predetermined point on said second plate, and for setting the distance between said second cam following means and a second predetermined point on said second plate, wherein said first and second linear cam surfaces are parallel to one another, said first and second arcuate surfaces have a common center lying equidistant from said first and second linear cam surfaces, the distance between said first and second linear cam surfaces being equal to the diameter of the circle containing said first and second arcuate surfaces plus the diameter of said cam following means;

a third plate mounted parallel to said first plate on the opposite side of said first plate from said second plate, having a third linear cam surface and a third arcuate cam surface for engaging said third cam following means, a fourth linear cam surface and fourth arcuate cam surface for engaging said fourth cam following means; means for setting the distance between said third cam following means and a third predetermined point on said third plate, and for setting the distance between said fourth cam following means and a fourth predetermined point on said third plate, wherein said third and fourth linear cam surfaces are parallel to one another, said third and fourth arcuate surfaces have a common center lying equidistant from said third and fourth linear cam surfaces, the distance between said third and fourth linear cam surfaces being equal to the diameter of the circle containing said third and fourth arcuate surfaces plus the diameter of said cam following means; and means for connecting said dental cast to said third plate.

7. The apparatus of claim 6 wherein each of said means for setting the distance between a cam following means and a predetermined point on the plate containing the cam surfaces engaged by said cam following means comprises a worm rotatable mounted on said plate and threadably engaged with said cam following means for displacing said plate relative to said cam following means upon rotation of said worm.

8. The apparatus of claim 5 wherein said posterior adjustment means comprises:

first and second linear members having adjustable lengths;

a fourth plate connected to said dental articulator by said first and second linear members and connected to said planar adjustment means, each of said linear members connecting a point on the posterior portion of said fourth plate to a point on said hinge axis; and an incisal support member for supporting the anterior portion of said fourth plate on the incisal table.

9. The apparatus of claim 8 wherein said anterior adjustment means comprises:

third and fourth linear members having adjustable lengths, each said third and fourth linear members connecting a point on the anterior portion of said planar adjustment means to said fourth plate, said connecting points being located substantially over two preselected points on said dental arch; and means for causing the plane of motion of said planar adjustment means to rotate about a point substantially on said hinge axis when the lengths of said third and fourth linear members is changed.

10. The apparatus of claim 9 wherein each of said third and fourth linear members comprises a worm rotatably connected to said planar adjustment means and threadably connected to said fourth plate.

11. The apparatus of claim 9 wherein each of said first and second linear members comprise a worm rotatably connected to said points on said hinge axis and threadably connected to said fourth plate.

12. The apparatus of claim 8 wherein said first and second linear members are mounted on a tangent of an arc centered about the end of said incisal support member which rests on said incisal table.

13. An apparatus for manipulating a dental cast including a dental arch representing the teeth for use in a dental articulator having a horizontal hinge axis and a base including an incisal table comprising:

a first plate including first, second, third, and fourth cam following means, said first and second cam following means having axes perpendicular to said first plate and protruding from the same side of said first plate, said axes substantially passing through said dental arch at first and second preselected points on said dental arch, third and fourth cam following means having axes perpendicular to said first plate and protruding from the opposite side of said first plate from said first and second cam following means and lying on a line which is perpendicular to the line joining said first and second cam following means, said third cam following means axis passing substantially through the center of the teeth of said dental arch, each of said cam following means having the same diameter;

a second plate mounted parallel to said first plate having a first linear cam surface and a first arcuate cam surface for engaging said first cam following means, a second linear cam surface and second arcuate cam surface for engaging said second cam following means; means for setting the distance between said first cam following means and a first predetermined point on said second plate, and for setting the distance between said second cam following means and a second predetermined point on said second plate, wherein said first and second linear cam surfaces are parallel to one another, said first and second arcuate surfaces have a common center lying equidistant from said first and second linear cam surfaces, the distance between said first and second linear cam surfaces being equal to the diameter of the circle containing said first and second arcuate surfaces plus the diameter of said cam following means;

a third plate mounted parallel to said first plate on the opposite side of said first plate from said second plate, having a third linear cam surface and a third arcuate cam surface for engaging said third cam following means, a fourth linear cam surface and fourth arcuate cam surface for engaging said fourth cam following means; means for setting the distance between said third cam following means and a third predetermined point on said third plate, and for setting the distance between said fourth cam following means and a fourth predetermined point on said third plate, wherein said third and fourth linear cam surfaces are parallel to one another, said third and fourth arcuate surfaces have a common center lying equidistant from said third and fourth linear cam surfaces, the distance between said third and fourth linear cam surfaces being equal to the diameter of the circle containing said third and fourth arcuate surfaces plus the diameter of said cam following means;

means for connecting said dental cast to said third plate;

first and second linear members having adjustable lengths;

a fourth plate connected to said dental articulator by said first and second linear members each of said linear members connecting a point on the posterior portion of said fourth plate to a point on said hinge axis; and an incisal support member for supporting the anterior portion of said fourth plate on the incisal table;

third and fourth linear members having adjustable lengths, said fourth plate being connected to said second plate by said third and fourth linear members each of said third and fourth linear members connecting a point on the anterior portion of said second plate to said fourth plate, said connecting points being located substantially over two preselected points on said dental arch; and extension means connected to said second plate and to said fourth plate by a fifth linear member having adjustable length for causing said second plate to rotate about a point substantially on said hinge axis when the lengths of said third and fourth linear members are changed.

14. The apparatus of claim 13 wherein each of said third and fourth linear members comprises a worm rotatably connected to said planar adjustment means and threadably connected to said fourth plate.

15. The apparatus of claim 13 wherein each of said first and second linear members comprise a worm rotatably connected to said points on said hinge axis and threadably connected to said fourth plate.

16. The apparatus of claim 13 wherein said first and second linear members are mounted on a tangent of an arc centered about the end of said incisal support member which rests on said incisal table.

17. A method for aligning either of the maxillary or mandibular dental casts comprising a model of a patient's teeth in a dental articulator and for recording the positional changes needed to bring said teeth in proper alignment comprising the steps of:
 (a) aligning the maxillary and mandibular dental casts in the positions representing the alignment of the teeth with respect to the patient's plane of occlusion before the proposed surgical adjustment;
 (b) replacing the dental cast which is not to be aligned with an occlusal table aligned on the occlusal plane of said patient's teeth as defined by the remaining dental cast;
 (c) marking the location of the remaining dental cast being aligned on said occlusal table including the vertical distances from selected teeth to said occlusal table;
 (d) rotating said remaining dental cast about one of a plurality of axes, each said axes being perpendicular to a substantially horizontal plane and passing through a preselected point on the dental arch on said cast until said teeth are in proper alignment;
 (e) marking the location of said dental cast on said occlusal table including the vertical distances from selected teeth to said occlusal table.

18. The method of claim 17 further comprising the step of rotating said dental cast about the hinge axis of said dental articulator until said teeth are in proper alignment.

19. The method of claim 17 further comprising the step of rotating said dental cast about an axis passing substantially through the center of said hinge axis until said teeth are in proper alignment.

20. The method of claim 17 further comprising the step of rotating said dental cast about an axis passing substantially through either the right or left row of teeth and said hinge axis until said teeth are in proper alignment.

* * * * *